United States Patent [19]

Bridger

[11] Patent Number: 4,582,920

[45] Date of Patent: Apr. 15, 1986

[54] METHOD OF MAKING A COPPER O,O-DIHYDROCARBYL PHOSPHORODITHIOATE

[75] Inventor: Robert F. Bridger, Hopewell, N.J.

[73] Assignee: Mobil Oil Corporation, New York, N.Y.

[21] Appl. No.: 642,926

[22] Filed: Aug. 21, 1984

[51] Int. Cl.[4] .............................................. C07F 1/08
[52] U.S. Cl. .................................................... 556/25
[58] Field of Search ........................ 260/438.1; 556/25

[56] References Cited

U.S. PATENT DOCUMENTS

| | | | |
|---|---|---|---|
| 2,552,570 | 5/1951 | McNab et al. | 260/438.1 X |
| 3,014,940 | 12/1961 | Lynch et al. | 260/438.1 X |
| 3,234,250 | 2/1966 | Schneider et al. | 260/438.1 X |
| 3,290,347 | 12/1966 | Miller | 260/438.1 X |
| 3,401,185 | 9/1968 | Meinhardt | 260/438.1 X |
| 3,426,054 | 2/1969 | Schneider et al. | 260/438.1 X |
| 3,428,662 | 2/1969 | Millendorf et al. | 260/438.1 X |
| 3,494,900 | 2/1970 | Morita et al. | 260/438.1 X |
| 3,773,815 | 11/1973 | Rossi et al. | 260/438.1 X |
| 3,984,448 | 10/1976 | Lippsmeier | 260/438.1 X |

*Primary Examiner*—Helen M. S. Sneed
*Attorney, Agent, or Firm*—Alexander J. McKillop; Michael G. Gilman; Van D. Harrison, Jr.

[57] ABSTRACT

A copper (1) dihydrocarbyl phosphordithioate is made by a method comprising reacting a bis(dihydrocarbyl phosphorothionyl) disulfide with activated copper metal.

9 Claims, No Drawings

METHOD OF MAKING A COPPER O,O-DIHYDROCARBYL PHOSPHORODITHIOATE

BACKGROUND OF THE INVENTION

1. Field of the Invention

The invention relates to a method of making a phosphorus acid copper salt. In particular, it relates to the copper salt of a phosphorodithioic acid.

2. Discussion of the Prior Art

Copper salts of phosphorodithioic acids are known compounds suitable for adding to lubricants, e.g., mineral lubricating oils, to impart oxidation resistant properties. For instance, see U.S. Pat. No. 2,552,570, which is incorporated herein by reference.

That same patent discloses that compounds of the type $$(RO)_2P(S)SCu$$

where R may be alkyl such as 2-ethylhexyl, and the like can be made by reacting, for example, a dialkyl phosphorodithioic acid with $Cu_2O$:

$$2(RO)_2P(S)SH + Cu_2O \rightarrow (RO)_2P(S)SCu + H_2O.$$

However, the salts made by this process are darkly colored products, indicative of contamination by divalent copper salts.

S. L. Lawton et al., *Inorganic Chemistry*, Vol. 11, No. 3, pages 612–618, 1972, teach a method of making copper (I) diisopropyl phosphorodithioate which comprises reacting an aqueous solution of cuprous chloride, containing sufficient ammonia to promote dissolution of the solid, with an aqueous solution of ammonium diisopropyl phosphorodithioate.

U.S. Pat. No. 2,552,570, incorporated herein by reference partly to establish utility of the compounds made by the improved method, describes the compositions used and the tests employed to establish utility.

SUMMARY OF THE INVENTION

In accordance with the invention, there is provided an improved method for making a Copper (I) dihydrocarbyl phosphorodithioate of the formula $$Cu_4[\overset{S}{\underset{\|}{S}P(OR)_2}]_4$$

wherein R is a hydrocarbyl group containing 1 to 24 carbon atoms, which may be the same or different, the improvement comprising reacting a bis(dihydrocarbyl phosphorothionyl)disulfide of the formula $$(RO)_2\overset{S}{\underset{\|}{P}}-S-S-\overset{S}{\underset{\|}{P}}(OR)_2$$

wherein R has the meaning already defined, with activated copper metal. The reaction may or may not be carried out in the presence of an inert solvent, depending upon the reactants and the products produced.

DESCRIPTION OF SPECIFIC EMBODIMENTS

The principal advantages of our improved process are that it yields a colorless product free of contamination by other reactants and which is also free of polymeric impurities and is colorless.

The reaction between the phosphorothionyl disulfide and activated copper can be carried out at from about 25° C. to about 120° C., preferably from about 40° C. to about 80° C., using equivalent amounts of reactants. I prefer, however, to use an excess of the activated copper. The amount of excess is not critical and can be easily judged by one having skill in this art. The reaction can be run using any solvent that does not take part in the reaction and from which the product can be easily recovered. These solvents include, but are not limited to, hexane, cyclohexane, benzene, toluene, xylene, hexadecane, lubricating oils, (mineral or synthetic).

Activated copper, used in this invention, is prepared by methods known to the art. For example, it may be prepared by the procedure of R. Q. Brewster and T. Groening, *Organic Synthesis Collective Volume* 2, page 446 (1943), incorporated herein by reference.

Procedures for preparing the phosphorothionyl disulfide used in the invention are also well known. One known method involves preparing a phosphorodithioic acid followed by oxidatively coupling two acid molecules to form the desired reactant. The reaction involved is shown in the equations $$P_2S_5 + 4ROH \longrightarrow 2(RO)_2P(S)SH + H_2S$$

$$2(RO)_2P(S)SH \xrightarrow{O_2} (RO)_2(PS)S-S-(S)P(OR)_2$$

The R group, which is coextensive with R in the product produced in this invention, is preferably an alkyl group. The alkyl group can be a straight or branched chain member and includes methyl, ethyl, propyl, isopropyl, butyl, 2-ethylhexyl, 4-methyl-2-pentyl, isodecyl, dodecyl, tetradecyl and octadecyl. Oxidation of the thioacid can take place in the presence of atmospheric oxygen or of other oxidants such as sodium hypochlorite, permanganate and the like.

Another known method one may use to prepare the phosphorothionyl disulfide is the following:

$$P_2S_5 + 4ROH \rightarrow 2(RO)_2P(S)SH + H_2S \quad (1)$$

$$(RO)_2P(S)SH + Na + \rightarrow (RO)_2P(S)SNa \quad (2)$$

$$PSCl_3 + 2ROH \rightarrow (RO)_2P(S)Cl + 2HCl \quad (3)$$

$$(RO)_2P(S)Cl + NaS(S)P(OR)_2 \rightarrow (RO)_2P(S)-S-S-(S)P(OR)_2 + NaCl \quad (4)$$

In which R is as already defined.

Reaction of the phosphorothionyl disulfide with copper proceeds as follows:

$$2(RO)_2P(S)-S-S-(S)P(OR)_2 + 4Cu \rightarrow Cu_4[S-(S)P(OR)_2]_4$$

I believe that a activated copper works because it has a very high surface area and the freshly prepared surface is relatively clear of impurities such as oxides and the like.

Having described the invention in general terms, the following specific examples are offered as illustrations. It will be understood that they are illustrations only, and that they are not meant to limit the invention.

EXAMPLE 1

Bis(O,O-diisopropylphosphorothionyl)disulfide (2.0 g, 4.69 mmol) was reacted with excess activated copper metal (5.96 g, 93.8 mmol) in 40 ml of hexane with vigorous stirring at reflux (68° C.) for 30 minutes. (The activated copper was prepared by the procedure of R. Q. Brewster and T. Groening, *Organic Synthesis, Collective Volume* 2, pages 446–447, 1943 incorporated herein by reference.) The solution was filtered and evaporated to yield 2.22 g (85% yield) of colorless, tetrameric copper(I) O,O-diisopropyl-phosphorodithioate, melting point 117°–118° C. Anal. Calcd. for $C_{24}H_{56}Cu_4O_8P_4S_8$: C, 26.03; H, 5.10; Cu, 22.96; P, 11.19; S, 23.16, mol wt., 1107. Found: C, 26.11; H, 5.01; Cu, 23.04; P, 11.18; S, 23.12, mol. wt. 1086. The phosphorus-31 NMR chemical shift in chloroform-d was 97.1 ppm. Carbon-13 NMR, chemical shift, ppm (carbon-phosphorus coupling, Hz): 23.70(5.1), 73.99(8.7).

EXAMPLE 2

Copper (I) O,O-dibutylphosphorodithioate, was prepared by reacting activated copper metal (7.9 g, 0.124 mol), prepared as in Example 1, with bis(O,O-dibutylphosphorothionyl)disulfide (5.0 g, 10.4 mmol) in 100 ml of refluxing hexane with stirring for 1 hour. Upon work-up, as in Example 1, 6.2 g (98% yield) of a colorless oil was obtained, which solidified on washing with hexane to give a colorless solid mp 99°–101° C. The phosphorus-31 NMR chemical shift of the product in chloroform-d was 100.20 ppm. Carbon-13 NMR, chemical shift, ppm (carbon-phosphorus coupling, Hz): 13.59, 18.80, 32.07(8.1), 68.36(8.1).

EXAMPLE 3

Copper(I) O,O-dimethylphosphorodithioate was prepared from activated copper metal (21.8 g, 0.343 mol) and bis(O,O-dimethylphosphorothionyl)disulfide (10.8 g, 0.0343 mol) in 200 ml of hexane following the procedure described as in Example 1. The product was insoluble in hexane and was extracted from the copper surface with benzene at 60° C. to yield 7.60 g (0.0344 mol, 50%) of a colorless solid which did not melt on heating, but decomposed at 155° C.

The phosphorus-31 NMR chemical shift in chloroform-d was 104.6 ppm. Carbon-13 NMR, chemical shift, ppm (carbon-phosphorus coupling, Hz): 54.94(7.3).

As is evident from this disclosure, reaction of activated copper with the phosphorothionyl disulfide proceeds as follows:

$$2(RO)_2P(S)-S-S-(S)P(OR)_2 + 4Cu \rightarrow Cu_4[S-(S)P(OR)_2]_4$$

I believe the activated copper provides about a 10-fold increase in rate of reaction when compared to regular copper because the former has a very high surface area which is relatively clear of impurities such as oxides and the like.

I claim:

1. An improved method for making a copper (I) dihydrocarbyl phosphorodithioate of the formula $$[(RO)_2\overset{\overset{S}{\|}}{P}S]_4Cu_4$$

wherein R is a hydrocarbyl group containing 1 to 24 carbon atoms, the improvement comprising reacting a bis(dihydrocarbyl phosphorothionyl)disulfide of the formula $$(RO)_2\overset{\overset{S}{\|}}{P}-S-S-\overset{\overset{S}{\|}}{P}(OR)_2$$

wherein R is as herein defined, with activated copper metal at a temperature from about 25° C. to about 125° C.

2. The method of claim 1 wherein the hydrocarbyl group is an alkyl group.

3. The method of claim 2 wherein the alkyl group is a methyl, ethyl, propyl, isopropyl, butyl, 4-methyl-2-pentyl, 2-ethylhexyl isodecyl, dodecyl, tetradecyl, or octacedyl group.

4. The method of claim 1 wherein the phosphorothionyl disulfide and activated copper are used in equivalent amounts.

5. The method of claim 1 wherein the activated copper is used in an amount in excess of the phosphorothionyl disulfide.

6. The method of claim 1 wherein the temperature is from about 40° C. to about 80° C.

7. The method of claim 1 wherein in the phosphorothionyl disufide R is methyl.

8. The method of claim 1 wherein in the phosphorothionyl disufide R is isopropyl.

9. The method of claim 1 wherein in the phosphorothionyl disufide R is butyl.

* * * * *